United States Patent [19]

Nisato et al.

[11] Patent Number: 4,514,408
[45] Date of Patent: Apr. 30, 1985

[54] N-SUBSTITUTED NICOTINAMIDE 1-OXIDE AS HISTAMINE $H_2$ RECEPTOR BLOCKERS

[75] Inventors: Dino Nisato, Pavia; Sergio Boveri, Tortona, both of Italy

[73] Assignee: Sanofi, Paris, France

[21] Appl. No.: 522,749

[22] Filed: Aug. 12, 1983

[30] Foreign Application Priority Data

Aug. 13, 1982 [FR] France ............... 82 14128
Apr. 22, 1983 [FR] France ............... 83 06681

[51] Int. Cl.³ .............. A61K 31/455; C07D 401/12
[52] U.S. Cl. ............... 514/212; 544/58.6; 544/131; 544/364; 544/365; 546/193; 546/194; 546/256; 546/261; 546/316; 514/222; 514/234; 514/318; 514/335; 514/343; 514/355
[58] Field of Search ............... 546/316, 261, 193, 194; 546/256; 544/58.6, 131, 364, 365; 424/266, 267, 248.54, 250, 246

[56] References Cited

U.S. PATENT DOCUMENTS 4,309,433 1/1982 Hirai et al. .............. 546/316 X

FOREIGN PATENT DOCUMENTS 0023578 2/1981 European Pat. Off. .......... 424/266
0024510 3/1981 European Pat. Off. .......... 546/233
978288 12/1964 United Kingdom ............ 546/316

OTHER PUBLICATIONS

Bickel, M., *Pharm. Rev.*, 21(4), p. 348, (1969).

*Primary Examiner*—Richard A. Schwartz
*Attorney, Agent, or Firm*—Stevens, Davis, Miller & Mosher

[57] ABSTRACT

N-substituted nicotinamide 1-oxide having histamine $H_2$ receptor blocking activity of formula

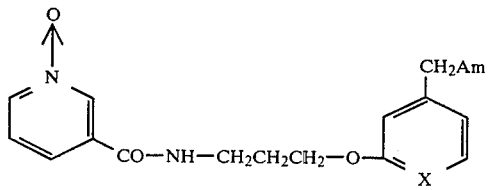

wherein X is a nitrogen atom or a CH group and Am represents a mono- or disubstituted amino group, a pyrrolidino, morpholino, thiomorpholino, hexamethyleneimino group, or an optionally substituted piperidino or piperazino group; their salts; a process for their preparation; and pharmaceutical compositions containing them as active ingredients.

7 Claims, No Drawings

N-SUBSTITUTED NICOTINAMIDE 1-OXIDE AS HISTAMINE $H_2$ RECEPTOR BLOCKERS

The present invention relates to novel nicotinamide 1-oxide derivatives having a histamine $H_2$ receptor blocking activity, to their salts, to a process for their preparation and to pharmaceutical compositions containing them as active ingredients.

More particularly, it is an objet of the present invention to provide N-substituted nicotinamide 1-oxide of formula

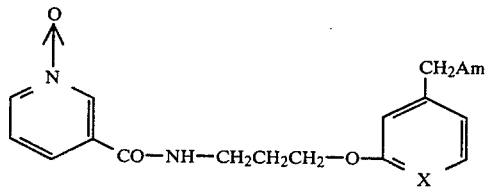

wherein X represents a nitrogen atom, or a CH group; Am represents an amino group substituted by lower alkyl, lower alkyl bearing a hydroxy or phenyl group or a cycloalkyl group of from 3 to 6 carbon atoms, or by a radical selected from the group consisting of lower alkenyl, lower alkynyl, phenyl and cycloalkyl of from 3 to 6 carbon atoms; an amino group substituted by two identical or different lower alkenyl or lower alkynyl groups; an amino group substituted by two identical or different (hydroxy)lower alkyl or (lower alkoxy)lower alkyl groups; a lower dialkylamino group; a lower dialkylamino group substituted by a phenyl, cycloalkyl of from 3 to 6 carbon atoms, methoxy or hydroxy group; a pyrrolidino group; a morpholino group; a thiomorpholino group; a hexamethyleneimino group; a piperidino group; a piperidino group substituted by a methyl, hydroxy or hydroxymethyl group or by two methyl groups; a piperazino group substituted in the 4-position by a lower alkyl group or a (hydroxy)lower alkyl group; a piperazino group substituted in the 4-position by a lower alkyl group or a (hydroxy)lower alkyl group and also bearing a methyl group in the 3 and/or 5-position; as well as its pharmaceutically acceptable salts.

The term "lower dialkylamino" as used herein designates the $NH_2$ group substituted by two identical or different lower alkyl groups.

The terms "lower alkyl", "lower alkenyl" and "lower alkynyl" as used herein designate an aliphatic hydrocarbon radical, saturated or containing a double or triple bond, having up to 4 carbon atoms.

The term "lower alkoxy" designates the hydroxy function in which the hydrogen atom is substituted by a lower alkyl group, as hereinabove defined.

The terms "pyrrolidino", "piperidino" and "piperazino", as used in the specification and in the claims, replace the nomenclature recommended by IUPAC for the radicals "1-pyrrolidinyl", "1-piperidinyl" and "1-piperazinyl", respectively.

The term "hexamethyleneimino" is used herein to designate the "1H-hexahydroazepin-1-yl" radical.

After the subdivision of histamine receptors into $H_1$ recpetors (Ash and Schild, Brit. J. Pharmac. Chemother. 1966, 27, 427) and $H_2$ receptors (Black et al., Nature 1972, 236, 385) and the discovery that the selective block of the $H_2$ receptors induces an inhibition of the gastric secretion, many products have been proposed as antagonists of the histamine $H_2$ receptors, hereinafter referred to as "$H_2$-blockers". Thus, the compounds having received the International Non-proprietary Names burimamide, metiamide, cimetidine, ranitidine, tiotidine, etintidine, oxmetidine have formed the subject matter of a large number of scientific publications.

All of the above-mentioned products are characterised by the presence in their molecule of the following structure:

wherein Z represents an oxygen or sulfur atom or an $N-CN$, $N-CO-$ or $CH-NO_2$ group, said structure being linear and bound to two aliphatic groups or included in a cycle as in the case of oxmetidine.

Cimetidine, 2-cyano-1-methyl-3-[2-[[(5-methylimidazol-4-yl)methyl]thio]ethyl]guanidine having the structure II where Z is $N-CN$ and ranitidine, N-[2-[[5-[(dimethylamino)methyl]furfuryl]thio]ethyl]-N'-methyl-2-nitro-1,1-ethenediamine, having the structure II where Z is $CH-NO_2$ are already used in therapy for the treatment of gastric and duodenal ulcer.

The European patent application No. 23 578 discloses derivatives of aminoalkylbenzene of formula

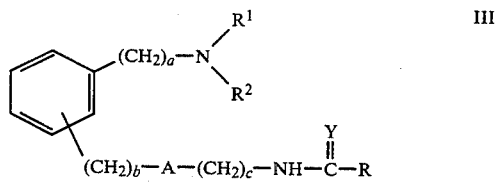

useful as $H_2$-blockers.

More particularly, said patent application indicates that the compounds of formula III, 1,3-disubstituted on the benzene ring, in which $NR^1R^2$ is pyrrolidino, a=1, b=0, A=oxygen, C=3, Y=oxygen and R is hydrogen or 3-pyridyl (compounds IV and V hereinbelow) possess an ED50 of 0.84 and, respectively, 1.25 mg/kg/i.v. in the test of the gastric hypersecretion according to Ghosh and Schild. It has now surprisingly been found that the compounds of formula I above, characterised by the presence of an amide of the nicotinic acid 1-oxide, possess an extraordinarily high and relatively long lasting $H_2$-blocking action.

The selective activity of the products of the present invention towards the receptors of type $H_2$ is confirmed by the absence of activity of type $H_1$ in the test of the contraction induced by histamine on the isolated guinea pig ileum.

The antagonistic activity of the compounds of the present invention towards the gastric histamine $H_2$ receptors has been confirmed in the test of the antisecretory activity based on the antagonism for the hypersecretion induced by histamine in the atropinised rat according to the method of Ghosh and Schild (Br. J. Pharmacol. Chemother. 1958, 13, 54) modified according to Black (Nature 1972, 236, 385). According to this test, a gastric acid hypersecretion is induced by intravenous infusion of a sub-maximal dose of histamine equivalent to 15 mcmol/kg/hour and the gastric secretion is measured by perfusion of a physiological solution at a constant speed in the stomach of the animal.

Cimetidine and ranitidine, which represent standard compounds, as well as:

the compound of formula $$\text{IV}$$

[Structure IV: benzene ring with CH$_2$N(pyrrolidine) substituent and O—CH$_2$CH$_2$CH$_2$NH—CO—H substituent]

as oxalate, and the compound of formula $$\text{V}$$

[Structure V: benzene ring with CH$_2$N(pyrrolidine) substituent and O—CH$_2$CH$_2$CH$_2$—NH—CO—(pyridine) substituent]

as dioxalate, both described in the above-cited European patent application No. 23 578, have been used as reference compounds.

The compounds of Examples 1, 2, 6 to 10 and 20 hereinbelow designated by their codes CM 57891, SR 58017A, SR 58062, SR 58037, SR 58042, SR 58067, SP 58052 and SR 58065 have been used as representative compounds of the invention.

Table I shows, for each product, the dose (in mcmol/kg by intravenous route in a single administration) which inhibits by 50% the gastric hypersecretion induced by histamine (ID50) as well as the relative potency as compared to cimetidine.

TABLE I

| Compound | ID50 (mcmol/kg) | Relative potency (cimetidine = 1) |
|---|---|---|
| Cimetidine | 0.95 | 1.00 |
| Ranitidine | 0.25 | 3.80 |
| Compound IV | 2.01 | 0.47 |
| Compound V | 2.22 | 0.43 |
| CM 57891 | 0.39 | 2.43 |
| SR 58017A | 0.11 | 8.64 |
| SR 58062 | 0.80 | 1.19 |
| SR 58037 | 0.13 | 7.31 |
| SR 58042 | 0.14 | 6.78 |
| SR 58067 | 0.71 | 1.34 |
| SR 58052 | 0.25 | 3.80 |
| SR 58065 | 0.64 | 1.48 |

It results from this table that all the representative compounds of the present invention have an extremely high activity, which, for two among them, is almost double that of ranitidine.

In comparison with the Compounds IV and V described in the European patent application No. 23 578, the compounds of the present invention show an up to 20 times higher antisecretory activity.

The compounds of formula I above, as well as their pharmaceutically acceptable salts, are prepared, according to a further object of the present invention, by a process comprising treating an amine of formula $$\text{VI}$$

[Structure VI: H$_2$N—CH$_2$CH$_2$CH$_2$—O—(benzene ring with X and CH$_2$Am substituents)]

wherein X and Am are as hereinabove defined, with a functional derivative of the nicotinic acid 1-oxide of $$\text{VII}$$

[Structure VII: pyridine N-oxide with COOH substituent]

in an organic solvent at a temperature of from 0° C. to the boiling temperature of the solvent employed and the product thus obtained is optionally converted into its pharmaceutically acceptable salts.

The activated free acid, the anhydride, a mixed anhydride, the chloride or an active ester may be used as a suitable functional derivative.

A preferred functional derivative of the acid of formula VII above is the chloride, preferably in the hydrochloride form, or an active ester of formula $$\text{VIII}$$

[Structure VIII: pyridine N-oxide with COOR° substituent]

wherein R° represents a nitrophenyl, methoxyphenyl, trityl or benzhydryl group.

The reaction temperature may vary from 0° C. to the boiling temperature of the solvent employed, but the operation is generally carried out at room temperature or at 30°–50° C. It may be preferable to carry out the reaction in a cold medium when it is exothermic, for example when the chloride is used as a functional derivative of the carboxylic acid of formula VII.

An alcohol, such as methanol or ethanol, or a halogenated solvent, such as methylene chloride, dichloroethane, chloroform and the like, is preferably used as a reaction solvent, but other organic solvents compatible with the reagents employed, for example acetonitrile, dioxane, tetrahydrofuran or a hydrocarbon such as hexane may also be used.

The reaction may be carried out in the presence of a proton acceptor, for example an alkaline carbonate or a tertiary amine, when hydrochloride acid, or another acid, forms during the reaction, but this proton acceptor is not critical for obtentionning of the final product.

The reaction is fairly rapid; after 1–4 hours at room temperature or at 30°–50° C. the reaction is over and the compound of formula I obtained is isolated according to conventional techniques in the form of free base or of one of its salts.

The free base may be converted into one of its pharmaceutically acceptable salts by treatment with a solution of the suitable acid in an organic solvent. If the compound I is isolated as a salt, the corresponding free base can be split off with an alcaline hydroxide or carbonate.

The starting compounds of formula VI above, in which X is CH, are known in the literature or may be easily prepared starting from 3-hydroxybenzaldehyde (IX) by reductive amination with the amine Am-H (X) by using sodium borohydride in methanol as reducing agent and by reacting the aminophenol (XI) thus obtained with 3-chloropropylamine hydrochloride in the presence of sodium hydride in dimethylformamide, according to the following scheme

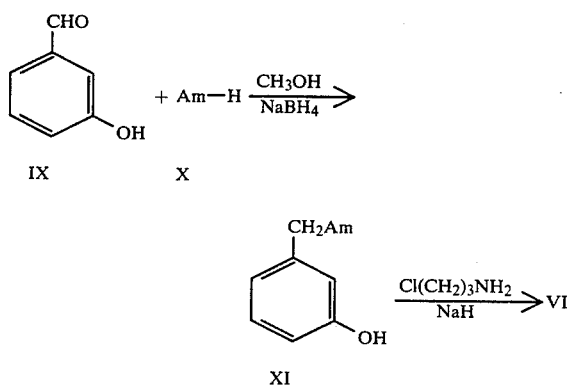

wherein Am is as hereinabove defined.

The starting compounds of formula VI above, in which X is N, are known or they may be prepared starting from the 2-chloroisonicotinic acid (XII) by converting it first into the acid chloride by action of thionyl chloride, then into the substituted amide (XIII) by reaction with the amine Am-H (X), by reacting the amide (XIII) thus obtained with 3-hydroxypropyl-2,5-dimethyl pyrrole, by subjecting the blocked amine (XIV) thus obtained to a reduction with lithium and aluminium hydride and finally, reacting the aminomethylpyridyloxypropyl pyrrole (XV) thus obtained with hydroxylamine hydrochloride in order to split off the amine VI, according to the following scheme

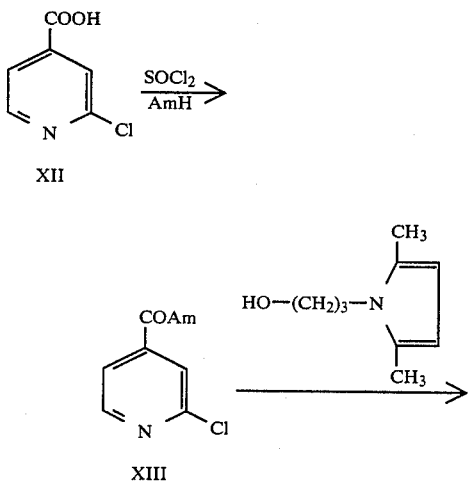

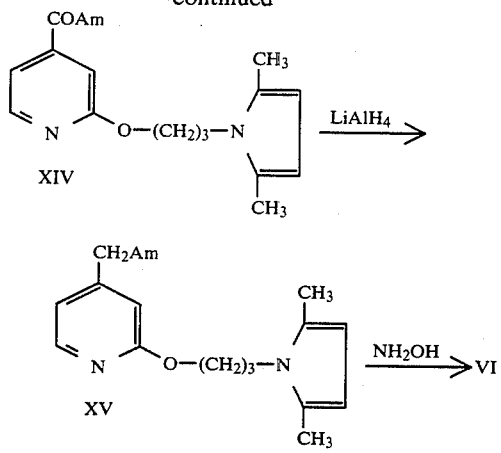

The compounds of formula VIII above are known in literature or they may be easily prepared by reacting the acid VII with the appropriate alcohol or phenol in the presence of a condensing agent such as dicyclohexylcarbodiimide in a solvent such as methylene chloride. The compounds of the present invention are only slightly toxic and are useful as drugs.

Thus, it is another object of the present invention to provide pharmaceutical compositions containing, as active ingredients, the compounds of formula I above, as well as their pharmaceutically acceptable addition salts.

In the pharmaceutical compositions of the present invention, for oral, sublingual, sub-cutaneous, intramuscular, intravenous, transdermic or rectal administration, the active ingredients of formula I above may be administered in unit forms of administration, in admixture with conventional pharmaceutical carriers, to animals and human beings for the treatment of gastric hypersecretion and ulcer disease. Appropriate unit forms of administration include the forms for oral administration, such as tablets, capsules, powders, granules and oral solutions or suspensions and the forms for sublingual and buccal administration, the forms for parenteral administration useful for a subcutaneous, intramuscular or intravenous injection, as well as the forms for rectal administration.

In order to obtain the desired antisecretory effect, the dose of active ingredient may vary between 0.1 and 100 mg per kg of body weight and per day.

Each unit dose may contain from 10 to 1000 mg, preferably from 50 to 500 mg, of active ingredient, in admixture with a pharmaceutical carrier. This unit dose may be administered from 1 to 4 times daily to treat the gastric hypersecretion and the ulcer disease.

The following examples illustrate the invention without, however, limiting it.

PREPARATION 1

(a) 3-morpholinomethylphenol

To a solution of 0.2 mol of 3-hydroxybenzaldehyde in 100 ml of methanol, is added, at about 20° C., a solution of 0.4 mol of morpholine in 40 ml of methanol. To the mixture thus obtained is added portionwise, under stirring at the temperature of 20°–25° C. within about 90 minutes, 0.2 mol of sodium borohydride, then the reaction mixture is stirred 3 hours at room temperature and the solvent is evaporated under reduced pressure to dryness. The residue is taken up with ice and acidified with hydrochloric acid, the acid solution is washed twice with 40 ml of ethyl acetate and concentrated ammonium hydroxide is added thereto up to clearly basic reaction. The mixture is extracted 4 times with 80 ml of ethyl acetate and the solvent is evaporated off. The product thus obtained melts at 113°–116° C. Yield: 67%.

(b) 3-(3-morpholinomethylphenoxy)propylamine

To a 80% suspension of 0.28 mol of sodium hydride in dimethylformamide, 0.06 mol of 3-morpholinomethylphenol is added portionwise, under stirring at a temperature of about 20° C., then the mixture is stirred 15 minutes at room temperature and a solution of 0.08 mol of 3-chloropropylamine hydrochloride in 20 ml of dimethylformamide is added thereto at 5°–10° C. The reaction mixture is stirred 24 hours at room temperature, then, after addition of 400 ml of ice-water, it is extracted 4 times with 100 ml of ethyl acetate. The organic solution is washed twice with 30 ml of 10% sodium hydroxide, then 3 times with 20 ml of water. The mixture is dried over anhydrous sodium sulfate and evaporated to dryness under reduced pressure. Thus, 3-(3-morpholinomethylphenoxy)propylamine is obtained, in the form of a yellow oil. Yield: 64%.

PREPARATION 2

3-(3-thiomorpholinomethylphenoxy)propylamine

By operating as described hereinabove, by reacting 0.2 mol of 3-hydroxybenzaldehyde with 0.4 mol of thiomorpholine in the presence of 0.2 mol of sodium borohydride (as in PREPARATION 1(a) 3-thiomorpholinomethylphenol is obtained, which, treated with an excess of 3-chloropropylamine hydrochloride in the presence of sodium hydride (as in PREPARATION 1(b), gives 3-(3-thiomorpholinomethylphenoxy)-propylamine, in the form of an oil.

PREPARATION 3

(a) 3-(4-hydroxypiperidinomethyl)phenol

To a solution of 0.2 mol of 3-hydroxybenzaldehyde in 100 ml of methanol, is added a solution of 0.4 mol of 4-hydroxypiperidine in 80 ml of methanol at about 20° C. To the mixture thus obtained 0.2 mol of sodium borohydride is added portionwise and under stirring, at the temperature of 20°–25° C. within about 90 minutes, then the reaction mixture is stirred 4 hours at room temperature and the solvent is evaporated under reduced pressure to dryness. The residue is taken up with ice and acidified with hydrochloric acid. The acid solution is washed twice with 40 ml of ethyl acetate and concentrated ammonium hydroxide is added thereto up to clearly basic reaction. The product which precipitates is filtered and crystallized from 400 ml of water. The product thus obtained melts at 156°–158° C. Yield: 66.8%.

(b) 3-/3-(4-hydroxypiperidinomethyl)phenoxy/propylamine

To a 50% suspension of 0.36 mol of sodium hydride in 180 ml of dimethylformamide, 0.14 mol of 3-(4-hydroxypiperidinomethyl)phenol is added portionwise, under stirring, at the temperature of about 20° C., then the mixture is stirred 15 minutes at 40° C., and afterwards a solution of 0.18 mol of 3-chloropropylamine hydrochloride in 80 ml of dimethylformamide is added thereto at 5°–10° C. The reaction mixture is stirred 24 hours at room temperaturem then 400 ml of ice-water containing hydrochloric acid is added thereto and the pH of the solution is adjusted to 6. The solution thus obtained is washed twice with 100 ml of ethyl acetate and made basic with concentrated sodium hydroxide. The resulting mixture is extracted 4 times with 80 ml of ethyl acetate, the organic phase is dried over anhydrous sodium sulfate and evaporated to dryness under reduced pressure. The oil thus obtained is chromatographied with methanol and, by evaporating the pure fraction, the product is isolated in the form of yellow oil. Yield: 16%.

PREPARATIONS 4 to 13

By operating as described hereinabove, by reacting 0.2 mol of 3-hydroxybenzaldehyde with 0.4 mol of piperidine, 4-methylpiperidine, 3-methylpiperidine, hexamethyleneimine, methylbenzylamine, 3-hydroxymethylpiperidine, 4-methylpiperazine, dimethylamine, di-n-propylamine and, respectively, di-n-butylamine in the presence of 0.2 mol of sodium borohydride (as in PREPARATION 3(a)), there is obtained the corresponding aminomethylphenols which, by treatment with an excess of 3-chloropropylamine hydrochloride in the presence of sodium hydride (as in PREPARATION 3(b) give the corresponding compounds of formula VI above.

The characteristics of the aminomethylphenols XI and of the intermediates VI thus obtained are summarized in TABLE II.

TABLE II

| Preparation | Am | Physico-chemical Characteristics | |
|---|---|---|---|
| | | Compound XI | Compound VI |
| 4 | −N⟨piperidine⟩ | m.p. 128–130° C. | m.p. 202–205° C. (dihydrochloride) |
| 5 | −N⟨piperidine⟩−CH₃ | pale yellow oil | m.p. 148–151° C. (dioxalate) |
| 6 | −N⟨piperidine with CH₃⟩ | m.p. 155–157° C. | yellow oil |
| 7 | −N⟨hexamethyleneimine⟩ | m.p. 116–118° C. | yellow oil |
| 8 | −N(CH₃)(CH₂−phenyl) | m.p. 206–211° C. (hydrochloride) | m.p. 147–149° C. (hydrochloride) |
| 9 | −N⟨piperidine−CH₂OH⟩ | oil | oil |

TABLE II-continued

| Preparation | Am | Physico-chemical Characteristics | |
|---|---|---|---|
| | | Compound XI | Compound VI |
| 10 | —N⟨ ⟩N—CH₃ (piperazine) | m.p. 255–258° C. (hydrochloride) | m.p. 253–255° C. (trihydrochloride) |
| 11 | —N(CH₃)₂ | m.p. 106–109° C. | m.p. 213–216° C. (dihydrochloride) |
| 12 | —N(nC₃H₇)₂ | m.p. 184–186° C. (hydrochloride) | m.p. 204–206° C. (dihydrochloride) |
| 13 | —N(nC₄H₉)₂ | m.p. 50–55° C. | oil |

PREPARATION 14

(a) 2-chloro-4-piperidinocarbonylpyridine

A mixture of 0.13 mol of 2-chloroisonicotinic acid and 70 ml of thionyl chloride is refluxed for 2 hours, then it is concentrated under reduced pressure and the residue is taken up with anhydrous toluene. The solvent is evaporated off and the crude 2-chloroisonicotinic acid chloride thus obtained in the form of a yellow solid is suspended in 50 ml of methylene chloride. The mixture is cooled to 0°–5° C. and a solution of 0.3 mol of piperidine in 50 ml of methylene chloride is added slowly thereto. The mixture is stirred two hours at room temperature, then washed thoroughly with water and the organic phase is evaporated to dryness. Thus, there is obtained 19 g of 2-chloro-4-piperidinocarbonylpyridine which is purified by chromatography on silica gel and elution with ethyl acetate. Thus, 10 g of a pure product in the form of a yellow oil are obtained.

(b) 2-[3-(2,5-dimethylpyrrol-1-yl)propoxy]-4-piperidinocarbonylpyridine

To a suspension of 0.047 mol of 2.5-dimethyl-1-(3-hydroxypropyl)pyrrole and 0.059 mol of 80% sodium hydride in 150 ml of 1,2-dimethoxyethane, previously heated at reflux for 15 minutes and cooled, is added 0.044 mol of 2-chloro-4-piperidino carbonylpyridine, then the reaction mixture is heated two hours with reflux and evaporated to dryness. The residue is taken up with water and extracted with ethyl acetate. The organic phase is separated and evaporated to dryness. Thus, 15.4 g of an oily product are obtained.

(c) 2-[3-(2,5-dimethylpyrrol-1-yl)propoxy]-4-piperidinomethylpyridine

A mixture of 15.4 g of the product thus obtained, 2 g of lithium and aluminium hydride and 150 ml of 1,2-dimethoxyethane is heated with reflux for 1 hour, then it is cooled and added with water slowly. The solution thus obtained is filtered and evaporated to dryness. The residue is taken up with water and acidified with N hydrochloric acid. The acid solution is washed twice with 30 ml of ethyl acetate, sodium hydroxide is added thereto to basic reaction and the solution is extracted 4 times with 30 ml of ethyl acetate. The organic phase is dried over anhydrous sodium sulfate and evaporated to dryness. Thus, 8.7 g of an oily product are obtained.

(d) 3-(4-piperidinomethylpyrid-2-yloxy)propylamine.

To a solution of 8.6 g of hydroxylamine hydrochloride in 26 ml of ethanol, stirred at the room temperature for 30 minutes, a solution of 2.8 g of 85% potassium hydroxide in 10 ml of 50% ethanol is added. The resulting solution is stirred 10 minutes and added with 8.7 g of 2-[3-(2,5-dimethylpyrrol-1-yl)propoxy]-4-piperidinomethylpyridine. The mixture is heated with reflux for 6 hours, filtered, washed with ethanol, acidified with N hydrochloric acid and washed twice with 30 ml of ethyl acetate. The pH of the aquoeus solution is adjusted to 8, then the solution is washed twice again with 30 ml of ethyl acetate and made clearly basic by addition of a concentrated solution of potassium hydroxide. The solution is extracted with ethyl acetate, the organic phase is dried over anhydrous sodium sulfate and the solvent is evaporated off. Thus, there is obtained 5.3 g of 3-(4-piperidinomethylpyrid-2-yloxy)propylamine as an oil.

PREPARATION 15

The 2-chloroisonicotinic acid is treated with thionyl chloride, then the chloride thus obtained is treated with dimethylamine (as described in PREPARATION 14(a) to obtain the dimethylamide of the 2-chloroisonicotinic acid, which, by condensation with 2,5-dimethyl-1-(3-hydroxypropyl)pyrrole in the presence of sodium hydride (as described in PREPARATION 14(b) gives the N,N-dimethyl-2-[3-(2,5-dimethylpyrrol-1-yl)propoxy]isonicotinamide (oil). The product thus obtained is reduced with lithium and aluminum hydride (as described in PREPARATION 14(c) and the 2-[3-(2,5-dimethylpyrrol-1-yl)propoxy]-4-dimethylaminomethylpyridine in split by the action of the hydroxylamine (as described in PREPARATION 14(d). The 3-(4-dimethylaminomethylpyrid-2-yloxy)propylamine is isolated as an oil.

PREPARATIONS 16 TO 33

By operating as described in PREPARATION 1, by reacting 0.2 mol of 3-hydroxybenzaldehyde with 0.2 mol of the appropriate amine in the presence of 0.2 mol of sodium borohydride and by treating the product thus obtained with 3-chloropropylamine hydrochloride in the presence of sodium hydride, there is obtained:
the 3-(3-butylaminomethylphenoxy)propylamine (16),
the 3-(3-allylaminomethylphenoxy)propylamine (17),
the 3-(3-propargylaminomethylphenoxy)propylamine (18),
the 3-[(2-hydroxyethyl)aminomethylphenoxy]propylamine (19),
the 3-(3-benzylaminomethylphenoxy)propylamine (20),
the 3-(3-cyclopropylmethylaminomethylphenoxy)propylamine (21),
the 3-(3-phenylaminomethylphenoxy)propylamine (22),
the 3-(3-cyclopentylaminomethylphenoxy)propylamine (23),
the 3-(3-diallylaminomethylphenoxy)propylamine (24),
the 3-(3-dipropargylaminomethylphenoxy)propylamine (25), the 3-[3-di(2-hydroxyethyl)aminomethylphenoxy]-propylamine (26),
the 3-[3-di(2-methoxyethyl)aminomethylphenoxy]-propylamine (27),
the 3-[(methyl-cyclopropylmethyl)aminomethylphenoxy]propylamine (28),
the 3-[4-(2-hydroxethylpiperazino)methylphenoxy]-propylamine (29),
the 3-(3,4,5-trimethylpiperazinomethylphenoxy)-propylamine (30),
the 3-(3,4-dimethylpiperazinomethylphenoxy)propylamine (31),
the 3-(3,5-dimethylpiperidinomethylphenoxy)propylamine (32) and,
the 3-[4-(2-hydroxyethyl)-3-methylpiperazinophenoxy]-propylamine (33).

EXAMPLE 1

To a mixture of 0.03 mol of 3-(3-pyrrolidinomethylphenoxy)propylamine and 0.095 mol of pyridine in 100 ml of methylene chloride, stirred at 0° C., 0.047 mol of nicotinic acid 1-oxide chloride hydrochloride is added portionwise, then the resulting mixture is stirred 1 hour at room temperature and the solvent is evaporated off under reduced pressure. The residue is taken up with N hydrochloric acid and the salts obtained are eliminated by filtration, then the solution is extracted 3 times with 100 ml of ethyl acetate and sodium hydroxide is added thereto up to a basic pH. The solution is extracted 4 times with 100 ml of ethyl acetate, the organic phase is dried over anhydrous sodium sulfate and the solvent is evaporated off under reduced pressure. The oil thus obtained is chromatographied on silica, and eluted with methanol, the fractions of the pure product are collected and the solution thus obtained is treated with a solution of oxalic acid in ethanol; the precipitate which forms is crystallized from ethanol to yield 3.5 g of N-[3-(3-pyrrolidinomethylphenoxy)propyl]3-pyridinecarboxamide 1-oxide sesquioxalate CM 57891A; m.p. 115°–116° C. Yield: 30% of the theoretical value.

Analysis for $C_{20}H_{25}N_3O_3$. 1.5 $C_2H_2O_4$: Calcd: C 56.32%, H 5.75%, N 8.57%. Found: 55.98%, 5.58%, N 8.38%.

One gram of the product thus obtained is suspended in concentrated sodium hydroxide, then the mixture is extracted with ethyl acetate and the organic solution is evaporated under reduced pressure to dryness. The residue crystallizes after 24–48 hours to give the N-[3-(3-pyrrolidinomethylphenoxy)propyl]-3-pyridinecarboxamide 1-oxide, CM 57891; m.p. 101°–103° C. Yield: 90% of the theoretical value.

Analysis for $C_{20}H_{25}N_3O_3$: Calcd: C 67.58%, H 7.09%, N 11.82%. Found: 67.01%, 7.02%, 11.68%.

EXAMPLES 2 TO 6

By operating as described in Example 1, by reacting 0.03 mol of 3-(3-piperidinomethylphenoxy)propylamine, of 3-(3-morpholinomethylphenoxy)propylamine, of 3-(3-dimethylaminomethylphenoxy)propylamine, of 3-(3-di-n-propylaminomethylphenoxy)propylamine and, respectively, of 3-(3-di-n-butylaminomethylphenoxy)propylamine with 0.047 mol of nicotinic acid 1-oxide chloride hydrochloride in methylene chloride, there is obtained:

the N-[3-(3-piperidinomethylphenoxy)propyl]-3-pyridinecarboxamide 1-oxide sesquioxalate, SR 58017A; m.p. 115°–118° C. (Ex. 2); yield: 30% of the theoretical value, Analysis for $C_{21}H_{27}N_3O_3$. 1.5 $C_2H_2O_4$: Calcd: C 57.13%, H 5.99%, N 8.33%. Found: 57.00%, 5.93%, 8.27%.

the N-[3-(3-morpholinomethylphenoxy)propyl]-3-pyridinecarboxamide 1-oxide sesquioxalate, SR 58016A; m.p. 152°–155° C. (Ex. 3); yield: 32% of the theoretical value, Analysis for $C_{20}H_{25}N_3O_4$. 1.5 $C_2H_2O_4$: Calcd: C 54.54%, H 5.57%, N 8.30%. Found: 54.26%, 5.66%, 8.18%.

the N-[3-(3-dimethylaminomethylphenoxy)propyl]-3-pyridinecarboxamide 1-oxide oxalate, SR 58059A; m.p. 148°–151° C. (Ex. 4); yield: 35% of the theoretical value, Analysis for $C_{18}H_{23}N_3O_3$. $C_2H_2O_4$: Calcd: C 57.27%, H 6.00%, N 10.02%. Found: 56.83%, 6.04%, 9.97%.

the N-[3-(3-di-n-propylaminomethylphenoxy)-propyl]-3-pyridinecarboxamide 1-oxide oxalate, SR 58030A; m.p. 168°–170° C. (Ex. 5); yield: 30% of the theoretical value, Analysis for $C_{22}H_{31}N_3O_3$. $C_2H_2O_4$: Calcd: C 60.62%, H 6.92%, N 8.84%. Found: 60.83%, 7.13%, 8.91%; and the N-[3-(3-di-n-butylaminomethylphenoxy)propyl]-3-pyridinecarboxamide 1-oxide, SR 58062; oil (Ex. 6); yield: 33% of the theoretical value, Analysis for $C_{24}H_{35}N_3O_3$: Calcd: C 69.70%, H 8.53%, N 10.16%. Found: 69.20%, 8.10%, 9.90%.

EXAMPLE 7

To a mixture of 0.023 mol of 3-[3-(4-methylpiperidinomethyl)phenoxy]propylamine and 30 ml of pyridine, stirred at 0° C., 0.047 mol of nicotinic acid 1-oxide chloride hydrochloride is added, portionwise; then the mixture is stirred for 1 hour at room temperature and the solvent is evaporated under reduced pressure. The residue is taken up with N hydrochloric acid and the salts thus obtained are eliminated by filtration, then the mixture is extracted 3 times with 100 ml of ethyl acetate and sodium hydroxide is added thereto to basic pH. The mixture is extracted with ethyl acetate containing 10% ethanol, the organic phase is dried over anhydrous sodium sulfate and the solvent is evaporated under reduced pressure. An oil which crystallizes slowly is obtained. The product is triturated in diethyl ether and filtered to give 4.5 g of crude product which is chromatographed on silica in a mixture methanol:chloroforme 15:35 and crystallized from ethyl acetate. Thus 2.7 g of N-[3-[3-(4-methylpiperidinomethyl)-phenoxy]propyl]-3-pyridinecarboxamide 1-oxide are obtained, SR 58037, m.p. 109°–111° C.; yield: 35% of the theoretical value.

Analysis for $C_{22}H_{29}N_3O_3$: Calcd: C 68.90%, H 7.62%, N 10.96%. Found: 68.69%, 7.85%, 11.11%.

EXAMPLES 8 AND 9

By operating as described in Example 7, by reacting 0.03 mol of 3-[3-(3-methylpiperidinomethyl)phenoxy]-propylamine and, respectively, of 3-[3-(4-hydroxypiperidinomethyl)phenoxy]propylamine with 0.047 mol of nicotinic acid 1-oxide chloride hydrochloride, there is obtained:

the N-[3-[3-(3-methylpiperidinomethyl)phenoxy]-propyl]-3-pyridinecarboxamide 1-oxide, SR 58042; m.p. 108°–110° C. (Ex. 8); yield: 35% of the theoretical value, Analysis for $C_{22}H_{29}N_3O_3$: Calcd: C 68.90%, H 7.62%, N 10.96%. Found: 68.72%, 7.81%, 10.91%; and the N-[3-[3-(4-hydroxypiperidinomethyl)phenoxy]-propyl]-3-pyridinecarboxamide 1-oxide, SR 58067; m.p. 113°–116° C. (Ex. 9); yield: 30% of the theoretical value, Analysis for $C_{21}H_{26}N_3O_4$: Calcd: C 65.44%; H 7.06%, N 10.90%. Found: 65.14%, 7.11%, 10.77%.

EXAMPLE 10

To a mixture of 0.03 mol of 3-(3-hexamethyleneiminomethylphenoxy)propylamine and 0.095 mol of pyridine in 100 ml of methylene chloride, stirred at 0° C., 0.047 mol of nicotinic acid 1-oxide chloride hydrochloride is added, portionwise, then the mixture is stirred for 90 minutes at room temperature and the solvent is evaporated under reduced pressure. By operating as described in Example 7, the N-[3-(3-hexamethyleneiminomethylphenoxy)propyl]-3-pyridinecarboxamide 1-oxide is obtained, SR 58052; m.p. 91°–93° C.; yield: 33% of the theoretical value.

Analysis for $C_{22}H_{29}N_3O_3$: Calcd: C 68.90%, H 7.62%, N 10.96%. Found: 69.00%, 7.89%, 11.06%.

EXAMPLES 11 TO 13

By operating as described in Example 7, by reacting 0.03 mol of 3-(3-benzylmethylaminomethylphenoxy)-propylamine, of 3-[3-(3-hydroxymethyl)piperidinomethylphenoxy]propylamine and, respectively, of 3-[3-(4-methylpiperazinomethyl)phenoxy]propylamine with 0.047 mol of nicotinic acid 1-oxide chloride hydrochloride in methylene chloride, there is obtained:

the N-[3-(3-benzylmethylaminomethylphenoxy)-propyl]-3-pyridinecarboxamide 1-oxide, SR 58083; m.p. 94°–96° C. (Ex. 11); yield: 30% of the theoretical value, Analysis for $C_{24}H_{27}N_3O_3$: Calcd: C 71.09%, H 6.71%, N 10.36%. Found: 70.87%, 6.75%, 10.19%.

the N-[3-[3-(3-hydroxymethyl)piperidinomethyl)phenoxy]propyl]-3-pyridinecarboxamide 1-oxide, SR 58087; as a vitreous solid (Ex. 12); yield: 20% of the theoretical value.

Analysis for $C_{25}H_{29}N_3O_4$: Calcd: C 68.94%, H 6.71%, N 9.65%. Found: 68.56%, 6.81%, 9.47%.

1H NMR (DMSO-d6): 3.2 ppm (m, $CH_2OH$); 4.0 ppm (~t, $ArOCH_2$); 8.55 ppm (~t, $2CHpyridine$); and the N-[3-[3-(4-methylpiperazinomethyl)phenoxy]-propyl]-3-pyridinecarboxamide 1-oxide, as a trihydrochloride, SR 58084A; m.p. 200°–205° C. (Ex. 13); yield: 45% of the theoretical value.

Analysis for $C_{21}H_{28}N_4O_3 \cdot 3HCl$: Calcd: C 51.07%, H 6.33%, N 8.51%. Found: 50.85%, 6.35%, 8.44%.

EXAMPLE 14

To a solution of 0.04 mol of 3-[3-(3-methyl-piperidinomethyl)phenoxy]propylamine in 40 ml of acetonitrile, 0.04 mol of the anhydride of the nicotinic acid 1-oxide is added (Synthesis, 1981, 618), then the reaction mixture is stirred for two hours at 50°–60° C. and evaporated to dryness under reduced pressure. The residue is taken up with 20 ml of concentrated sodium hydroxide and extracted 4 times with 30 ml of ethyl acetate. The organic phase is dried over anhydrous sodium sulfate, the solvent is evaporated under reduced pressure and the product thus obtained is purified by chromatography on silica as described in Example 7. Thus, the N-[3-[3-(3-methylpiperidinomethyl)phenoxy]propyl]-3-pyridinecarboxamide 1-oxide, identical to the product of Example 8 is obtained; m.p. 108°–110° C.

EXAMPLE 15

To a solution of 0.03 mol of nicotinic acid 1-oxide in 40 ml of methylene chloride containing 10 ml of triethylamine, is added, at the temperature of from 0° to 5° C. and within about 10 minutes, 0.03 mol of isobutyl chloroformate dissolved in 15 ml of methylene chloride, then the mixture is stirred 30 minutes at the same temperature. To the same mixture and at the same temperature there is added 0.03 mol of 3-[3-(3-methyl-piperidinomethyl)phenoxy]propylamine dissolved in 15 ml of methylene chloride, then, after a 2 hours stirring at room temperature, the reaction mixture is washed with 10 ml of water. The organic phase is filtered, dried over anhydrous sodium sulfate and evaporated to dryness under reduced pressure. The residue is purified by chromatography on silica as described in Example 7 to yield the N-[3-[3-(3-methylpiperidinomethyl)phenoxy]-propyl]-3-pyridinecarboxamide 1-oxide, identical to the product of Example 8.

EXAMPLE 16

To a solution of 11.6 G of nicotinic acid 1-oxide, 11.2 g of 4-nitrophenol and 8.2 g of triethylamine in 160 ml of methylene chloride there is added 17.6 g of benzotriazolyloxy-tris-(dimethylamino)phosphonium hexafluorophosphate. The temperature of the mixture rises and a solution is obtained from which the active ester separates. The mixture is stirred for additional 30 minutes, then the precipitate is filtered and washed first with methylene chloride then with diethyl ether. Thus, there is obtained 4 g of 4-nitrophenyl 3-pyridinecarboxylate 1-oxide; m.p. 234°–236° C. (dec.).

To the active ester thus obtained there is added a solution of 3.8 g of 3-[3-(3-methylpiperidinomethyl)-phenoxy]propylamine in 70 ml of methanol and the mixture is stirred 3 hours at 50° C. The solvent is evaporated, the residue is taken up with 30 ml of N hydrochloric acid and the acid solution is washed 3 times with 20 ml of ethyl acetate. The pH is adjusted to 7.8, then the solution is salted out with sodium chloride and extracted 6 times with 30 ml of ethyl acetate. The organic extracts are collected and dried over anhydrous sodium sulfate and the solvent in evaporated to dryness. The product is purified by chromatography on silica as described in Example 7. Thus, the N-[3-[3-(3-methyl-piperidinomethyl)phenoxy]propyl]-3-pyridinecarboxamide 1-oxide is obtained, identical to the product of Example 8.

EXAMPLE 17

To a solution of 5 g of 4-dimethylaminopyridine in 80 ml of acetonitrile there is added 5.6 g of nicotinic acid 1-oxide. The mixture is stirred 10 minutes at room temperature and then added with 9.2 g of dicyclohexylcarbodiimide. After standing 5 minutes at room temperature, there are added 10 g of 3-[3-(methylpiperidinomethyl)phenoxy]propylamine dissolved in 20 ml of acetonitrile. A weakly exothermic reaction (from 20° to 25° C.) and a dissolution which within 5 minutes is almost completed, are observed. Then the mixture is stirred 4 hours at 40° C. and the dicyclohexylurea which forms is filtered and washed with acetonitrile. After evaporation to dryness under reduced pressure, the residue is purified by chromatography on silica as described in Example 7. Thus, the N-[3-[3-(3-methylpiperidinomethyl)-phenoxy]propyl]-3-pyridinecarboxamide 1-oxide is obtained, identical to the product of Example 8; m.p. 108°–110° C.

EXAMPLE 18

To a suspension of 2.8 g of nicotinic acid 1-oxide, 2.5 g of dimethylaminopyridine, 8.8 g of benzotriazolyloxy-tris-(dimethylamino)phosphonium hexafluorophosphate in 40 ml of acetonitrile, 5 g of 3-[3-(3-methyl-piperidinomethyl)phenoxy]propylamine dissolved in 10 ml of acetonitrile are added at 20° C. under stirring. A rising of the temperature up to 30° C. is observed and a solution is obtained which is then stirred 2 hours at room temperature. The mixture is concentrated under reduced pressure, the residue is treated with 20 ml of concentrated sodium hydroxide and extracted 4 times with 40 ml of ethyl acetate. After evaporation of the organic extracts, the residue is purified by chromatography on silica as described in Example 7. Thus, the N-[3-[3-(3-methylpiperidinomethyl)phenoxy]propyl]-3-pyridinecarboxamide 1-oxide is obtained, identical to the product of Example 8.

EXAMPLE 19

To a mixture of 0.03 mol of 3-(4-dimethylaminomethylpyrid-2-yloxy)propylamine and 0.095 mol of pyridine in 100 ml of methylene chloride, stirred at 0° C., 0.047 mol of nicotinic acid 1-oxide chloride hydrochloride is added portionwise, then the mixture is stirred for 90 minutes at room temperature and the solvent is evaporated under reduced pressure. By operating as described in Example 1, the N-[3-(4-dimethylaminomethylpyrid-2-yloxy)propyl]-3-pyridinecarboxamide 1-oxide sesquioxalate is obtained.

By neutralising the product thus obtained with sodium hydroxide, the N-[3-(4-dimethylaminomethylpyrid-2yloxy)propyl]-3-pyridinecarboxamide 1-oxide is obtained, SR 58098; m.p. 103°–106° C.

Analysis for $C_{17}H_{22}N_4O_3$: Calcd: C 61.80%, H 6.71%, N 17.04%. Found: 61.21%, 6.78%, 16.97%.

EXAMPLES 20 AND 21

By operating as described in Example 7, by reacting 0.03 mol of 3-(4-piperidinomethylpyrid-2-yloxy)-propylamine and, respectively, of 3-(4-dimethylaminomethylpyrid-2-yloxy)propylamine with 0.047 mol of nicotinic acid 1-oxide chloride hydrochloride there is obtained:

the N-[3-(4-piperidinomethylpyrid-2-yloxy)propyl]3-pyridinecarboxamide 1-oxide, SR 58065; m.p. 87°–89° C. (Ex. 20); yield: 35% of the theoretical value, Analysis for $C_{20}H_{26}N_4O_3$: Calcd: C 64.84%, H 7.07%, N 15.12%. Found: 64.98%, 7.16%, 15.14%, and the N-[3-(4-dimethylaminomethylpyrid-2-yloxy)-propyl]3-pyridinecarboxamide 1-oxide, SR 58098; m.p. 103°–106° C. (Ex. 21) identical to the product of Example 19; yield: 35% of the theoretical value.

EXAMPLES 22 TO 39

By operating as described in Example 16, by reacting 0.03 mol of 3-(3-butylaminomethylphenoxy)propylamine, of 3-(3-allylaminomethylphenoxy)propylamine, of 3-(3-propargylaminomethylphenoxy)propylamine, of 3-[(2-hydroxyethyl)aminomethylphenoxy]propylamine, of 3-(3-benzylaminomethylphenoxy)propylamine, of 3-(3-cyclopropylmethylaminomethylphenoxy)propylamine, of 3-(3-phenylaminomethylphenoxy)propylamine, of 3-(3-cyclopentylaminomethylphenoxy)-propylamine, of 3-(3-diallylaminomethylphenoxy)-propylamine, of 3-(3-dipropargylaminomethylphenoxy)propylamine, of 3-[3-di(2-hydroxyethyl)aminomethylphenoxy]propylamine, of 3-[3-di(2-methoxyethyl)aminomethylphenoxy]propylamine, of 3-[(methylcyclopropylmethyl)aminomethylphenoxy]propylamine, of 3-[4-(2-hydroxyethylpiperazino)methylphenoxy]-propylamine, of 3-(3,4,5-trimethylpiperazinomethylphenoxy)propylamine, of 3-(3,4-dimethylpiperazinomethylphenoxy)propylamine, of 3-(3,5-dimethylpiperidinomethylphenoxy)propylamine and, respectively of 3-[4-(2-hydroxyethyl)-3-methylpiperazinomethylphenoxy]propylamine with 0.03 mol of 4-nitrophenyl 3-pyridinecarboxylate 1-oxide there is obtained:

the N-[3-(3-butylaminomethylphenoxy)propyl]-3-pyridinecarboxamide 1-oxide (Ex. 22);

the N-[3-(3-allylaminomethylphenoxy)propyl]-3-pyridinecarboxamide 1-oxide (Ex. 23);

the N-[3-(3-propargylaminomethylphenoxy)propyl]-3-pyridinecarboxamide 1-oxide (Ex. 24);

the N-[3-[(2-hydroxyethyl)aminomethylphenoxy]-propyl]-3-pyridinecarboxamide 1-oxide (Ex. 25);

the N-[3-(3-benzylaminomethylphenoxy)propyl]-3-pyridinecarboxamide 1-oxide (Ex. 26);

the N-[3-(3-cyclopropylmethylaminomethylphenoxy)propyl]3-pyridinecarboxamide 1-oxide (Ex. 27);

the N-[3-(3-phenylaminomethylphenoxy)propyl]-3-pyridinecarboxamide 1-oxide (Ex. 28);

the N-[3-(3-cyclopentylaminomethylphenoxy)-propyl]-3-pyridinecarboxamide 1-oxide (Ex. 29);

the N-[3-(3-diallylaminomethylphenoxy)propyl]-3-pyridinecarboxamide 1-oxide (Ex. 30);

the N-[3-(3-dipropargylaminomethylphenoxy)-propyl]-3-pyridinecarboxamide 1-oxide (Ex. 31);

the N-[3-[3-di(2-hydroxyethyl)aminomethylphenoxy]propyl]3-pyridinecarboxamide 1-oxide (Ex. 32);

the N-[3-[3-di(2-methoxyethyl)aminomethylphenoxy]propyl]3-pyridinecarboxamide 1-oxide (Ex. 33);

the N-[3-[(methyl-cyclopropylmethyl)aminomethylphenoxy]-propyl]-3-pyridinecarboxamide 1-oxide (Ex. 34);

the N-[3-[4-(2-hydroxyethylpiperazino)methylphenoxy]-propyl]-3-pyridinecarboxamide 1-oxide (Ex. 35);

the N-[3-(3,4,5-trimethylpiperazinomethylphenoxy)-propyl]3-pyridinecarboxamide 1-oxide (Ex. 36);

the N-[3-(3,4-dimethylpiperazinomethylphenoxy)-propyl]-3-pyridinecarboxamide 1-oxide (Ex. 37);

the N-[3-(3,5-dimethylpiperidinomethylphenoxy)-propyl]-3-pyridinecarboxamide 1-oxide (Ex. 38); and, respectively, the N-[3-[4-(2-hydroxyethyl)-3-methylpiperazinomethylphenoxy]propyl]-3-pyridinecarboxamide 1-oxide (Ex. 39).

EXAMPLE 40

Tablets comprising one of the products described in Examples 1 to 12 and 18 to 39, having the following composition:

| | |
|---|---|
| active substance | 150 mg |
| microcrystalline cellulose | 75 mg |
| talc | 15 mg |
| polyvinylpyrrolidone | 30 mg |
| precipitated silica | 25 mg |
| magnesium stearate | 5 mg |

All the ingredients, except the lubricant, are intimately mixed in a mixing machine for 15 minutes, then the mixture is binded by gradual addition of water. The mass is passed through a 1.25 mm sieve. The granules are dried in a fluidized bed dryer until a proper wetness is obtained (about 2% water). To the uniform mass there is added the lubricant and tablets are prepared by compression. Weight of a tablet: 300 mg.

In the same manner, tablets comprisng 250 mg of active substance are prepared.

We claim:

1. A N-substituted nicotinamide 1-oxide of formula

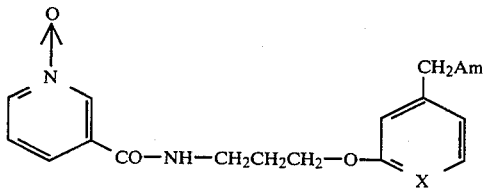

wherein X represents a nitrogen atom or a CH group; Am represents an amino group substituted by lower alkyl, lower alkyl bearing a hydroxy or phenyl group or a cycloalkyl group of from 3 to 6 carbon atoms, or by a radical selected from the group consisting of lower alkenyl, lower alkynyl, phenyl and cycloalkyl of from 3 to 6 carbon atoms; an amino group substituted by two identical or different lower alkenyl or lower alkynyl groups; an amino group substituted by two identical or different (hydroxy)lower alkyl or (lower alkoxy)lower alkyl groups; a lower dialkylamino group; a lower dialkylamino group substituted by a phenyl, cycloalkyl of from 3 to 6 carbon atoms, methoxy or hydroxy group; a pyrrolidino group; a morpholino group; a thiomorpholino group; a hexamethyleneimino group; a piperidino group; a piperidino group substituted by a methyl, hydroxy or hydroxymethyl group or by two methyl groups; a piperazino group substituted in the 4-position by a lower alkyl group or a (hydroxy)lower alkyl group; a piperazino group substituted in the 4-position by a lower alkyl group or a (hydroxy)lower alkyl group and also bearing a methyl group in the 3- and/or 5-position; or a pharmaceutically acceptable acid addition salt thereof.

2. The N-[3-[3-(3-methylpiperidinomethyl)phenoxy]-propyl]-3-pyridinecarboxamide 1-oxide or a pharmaceutically acceptable acid addition salt thereof.

3. The N-[3-[3-(4-methylpiperidinomethyl)phenoxy]-propyl]-3-pyridinecarboxamide 1-oxide or a pharmaceutically acceptable acid addition salt thereof.

4. The N-[3-[3-(4-hydroxypiperidinomethyl)phenoxy]propyl]-3-pyridinecarboxamide 1-oxide or a pharmaceutically acceptable acid addition salt thereof.

5. The N-[3-(3-hexamethyleneiminomethylphenoxy)-propyl]-3-pyridinecarboxamide 1-oxide or a pharmaceutically acceptable acid addition salt thereof.

6. A pharmaceutical composition in dosage unit form having histamine $H_2$-blocking action comprising from 10 to 1000 mg of a compound as claimed in one of claims 1 to 5 in admixture with a pharmaceutical carrier.

7. A composition as claimed in claim 6 comprising from 50 to 500 mg of a compound as claimed in one of claims 1 to 5.

* * * * *